US00PP29256P3

(12) United States Plant Patent
Stemkens

(10) Patent No.: US PP29,256 P3
(45) Date of Patent: Apr. 24, 2018

(54) ***SAXIFRAGA* PLANT NAMED 'SAXZ0013'**

(50) Latin Name: *Saxifraga×arendsii*
Varietal Denomination: SAXZ0013

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/330,066

(22) Filed: Aug. 1, 2016

(65) Prior Publication Data

US 2016/0360669 P1 Dec. 8, 2016

Related U.S. Application Data

(60) Provisional application No. 62/252,750, filed on Nov. 9, 2015.

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

(56) References Cited

PUBLICATIONS

PLUTO: Plant Variety Database, Sep. 9, 2017, citation for 'SAXZ0013'. 1 page.*

* cited by examiner

*Primary Examiner* — Susan McCormick Ewoldt
*Assistant Examiner* — Karen M Redden
(74) *Attorney, Agent, or Firm* — Dale Skalla

(57) ABSTRACT

A new *Saxifraga* plant named 'SAXZ0013' particularly distinguished by its red coloured flowers with green leaves on a mounding compact round and well branched plant habit that starts to flower quite late.

1 Drawing Sheet

Latin name of the genus and species of the plant claimed: *Saxifraga×arendsii.*

Varietal denomination: 'SAXZ0013'.

BACKGROUND OF THE NEW PLANT

The present invention comprises a new *Saxifraga*, botanically known as *Saxifraga×arendsii*, and hereinafter referred to by the variety name 'SAXZ0013'.

'SAXZ0013' is a product of a planned breeding program. The new cultivar 'SAXZ0013' has red colored flowers with green leaves on a mounding compact round and well branched plant habit that starts to flower quite late.

'SAXZ0013' originates from an open hybridization made in a greenhouse in April 2009 in Enkhuizen, The Netherlands. The female parent was an unpatented, proprietary plant identified as 'SX015' with smaller, darkred color that blackens with aging and is later to flower when compared to 'SAXZ0013'.

The male parent of 'SAXZ0013' is unknown. The resultant seed was sown in August 2009 in Enkhuizen, The Netherlands.

'SAXZ0013' was selected as one flowering plant within the progeny of the stated cross in March 2010 in a greenhouse in Enkhuizen, The Netherlands.

The first act of asexual reproduction of 'SAXZ0013' was accomplished when vegetative cuttings were propagated from the initial selection in March 2010 in a greenhouse in Enkhuizen, The Netherlands.

BRIEF SUMMARY OF INVENTION

Horticultural examination of plants grown from cuttings of the plant initiated in June 2010 in Enkhuizen, The Netherlands, and continuing thereafter, has demonstrated that the combination of characteristics as herein disclosed for 'SAXZ0013' are firmly fixed and are retained through successive generations of asexual reproduction.

'SAXZ0013' has not been observed under all possible environmental conditions. The phenotype may vary significantly with variations in environment such as temperature, light intensity and day length.

A Plant Breeder's Right for this cultivar was applied for in the European Union on Jun. 4, 2015, No. 2015/1164. 'SAXZ0013' has not been made publicly available prior to the effective filing date of this application, notwithstanding any disclosure that may have been made less than one year prior to the effective filing date of this application by the inventor or another who obtained 'SAXZ0013' directly from the inventor.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawings show typical flower and foliage characteristics of 'SAXZ0013' with colors being as true as possible with an illustration of this type.

Figure 1:
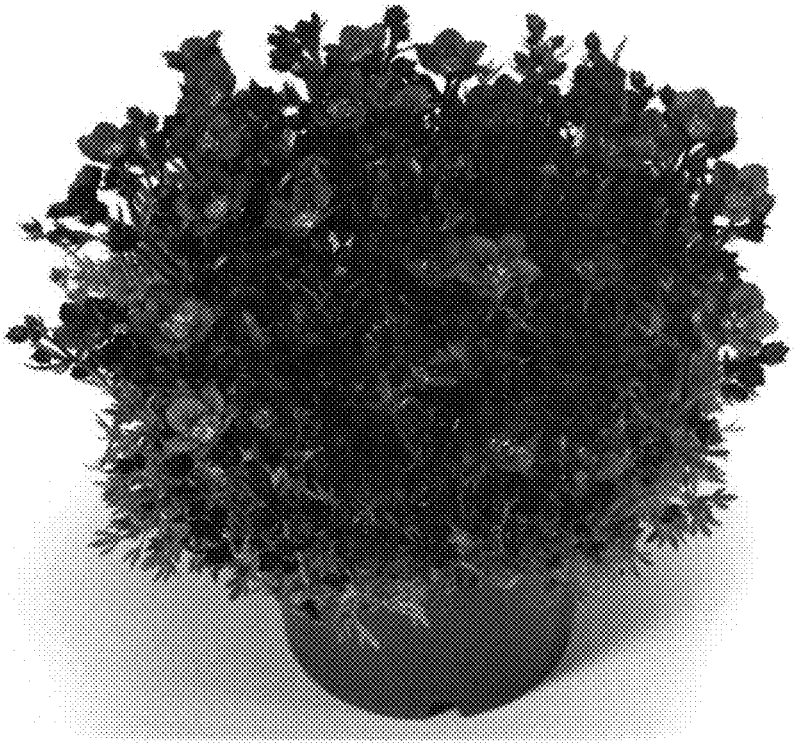
Figure 2:
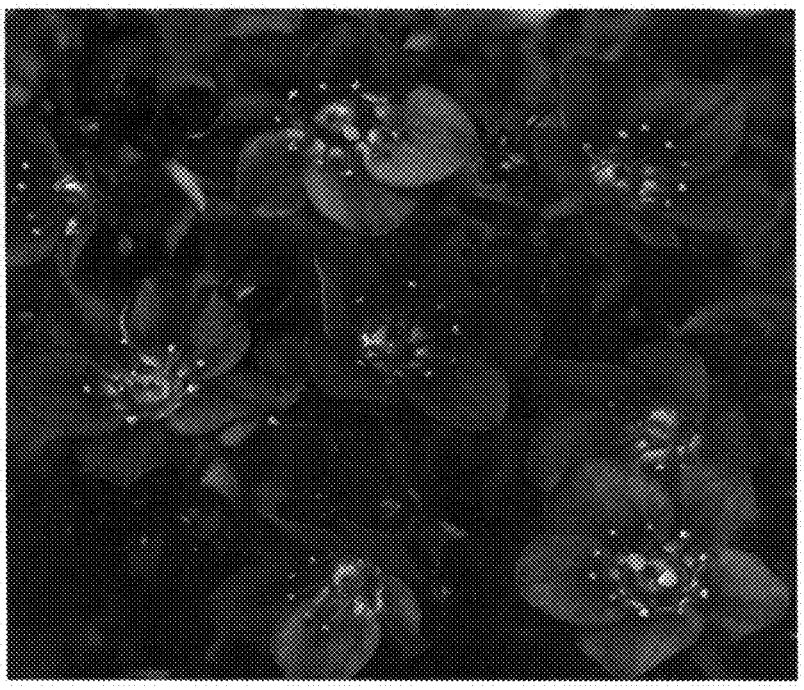

The photographic drawings show in FIG. 1 a flowering plant of the new variety and in FIG. 2 a close-up of the flowers.

DETAILED BOTANICAL DESCRIPTION

The plant descriptions and measurements were taken in Enkhuizen, The Netherlands under natural light in March 2015. These plants were approximately 36 weeks old and were growing in 11 cm pots in poly covered tunnels outdoors. The plants used for the photographs were about 36 weeks old growing in Enkhuizen, The Netherlands and the photographs were taken in March 2015.

Color chart used: Royal Horticultural Society Colour Chart (R.H.S.) 2001

TABLE 1

DIFFERENCES BETWEEN THE NEW VARIETY 'SAXZ0013' AND A SIMILAR VARIETY

| | 'SAXZ0013' | 'ROCKRED', U.S. Plant Pat. No. 19,643 |
|---|---|---|
| Flowering: | Early flowering (1 week earlier) | Later flowering |
| Plant habit: | Compact, round | Very compact, slow growth |
| Flower color: | Clear deepred | Deep red that blackens when aging |

Plant:

*Form, growth and habit*.—A rosetting habit that is compact and mounded. Each rosette develops several short branched peduncles that are freely flowering.

*Plant height*.—7-8 cm.

*Plant height (inflorescence included)*.—12-13 cm.

*Plant width*.—18 cm.

Roots:

*Number of days to initiate roots*.—About 7 days at about 18 degrees C.

*Number of days to produce a rooted cutting*.—3 weeks at 18 degrees C.

*Type*.—Fine, fibrous, well branched.

*Color*.—RHS N155B but whiter.

Foliage:

*Arrangement*.—Rosulate, alternate.

*Immature, leaf color, upper surface*.—RHS 143A.

*Immature, lower surface*.—RHS 141C.

*Mature, leaf color, upper surface*.—RHS 141B.

*Mature, leaf color, lower surface*.—RHS 141C.

*Length*.—1.5-2.0 cm.

*Width*.—1.5 cm.

*Shape*.—Cunneate; 3 to 5 cleft-lobed.

*Base shape*.—Attenuate, sessile.

*Apex shape*.—Tridentate.

*Margin*.—Entire, laciniate.

*Texture, upper surface*.—Glabrous.

*Lower surface*.—Glabrous.

*Color of veins, upper surface*.—Indistinct.

*Color of veins, lower surface*.—Indistinct.

*Petiole color*.—RHS 143B+C.

*Length*.—0.3-1.0 cm.

*Diameter*.—0.1-0.3 cm.

*Texture*.—Glabrous, but on the edge hirsute.

Lateral branching:

*Color*.—RHS 142C.

*Length of branch*.—3.0-4.0 cm.

*Diameter of branch*.—0.2-0.3 cm.

*Texture*.—Hirsute.

*Color of peduncle*.—RHS 142B.

*Length of peduncle*.—6.0-9.0 cm.

*Peduncle diameter*.—0.1 cm.

*Texture*.—Glandular and puberulous.

*Pedicel color*.—Near to RHS 141B.

*Pedicel length*.—1.0 cm.

*Pedicel diameter*.—0.1 cm.

*Pedicel texture*.—Glandular and puberulous.

Inflorescence:

*Type*.—Simple cyme or raceme, each inflorescence consists of 15-25 single flowers; single flower composed of 5 imbricate petals; flowers held above the plant.

*Quantity of inflorescences per plant*.—100-150 with numerous buds.

*Lastingness of individual blooms on the plant*.—About 11 days.

*Fragrance*.—None.

Bud (just before opening/showing color):

*Color*.—RHS 59A.

*Length*.—0.8 cm.

*Width*.—0.5 cm.

*Shape*.—Conical, penta-shape.

Corolla:

Immature inflorescence:

*Diameter*.—1.5 cm.

*Color of petals, upper surface*.—Nearest to RHS 60A.

*Lower surface*.—RHS 60A.

Mature inflorescence:

*Flower diameter*.—1.8-2.2 cm.

*Depth*.—1-1.2 cm.

*Petal color, upper surface*.—Nearest to RHS 60A.

*Petal color, lower surface*.—RHS 60A.

*Veins color, upper surface*.—Darker than RHS 60A.

*Veins color, lower surface*.—Darker than RHS 60A.

*Length of petal*.—1.0 cm.

*Width of petal*.—1.0 cm.

*Shape*.—Orbicular, round to obovate.

*Apex shape*.—Ovate to obovate, almost 100% round.

*Margin*.—Entire.

*Venation pattern*.—Bowed, parallel.

*Petal texture, upper surface*.—Glabrous.

*Petal texture, lower surface*.—Glabrous.

Calyx:

*Quantity*.—5.

*Color, upper surface*.—Darker than RHS 59A.

*Color, lower surface*.—RHS 147C.

*Length*.—0.5 cm.

*Width*.—0.2 cm.

*Shape*.—Hastate, subulate.

*Apex shape*.—Acute.

*Base*.—Fused, deltoid.

*Margins*.—Entire.

*Texture, upper/inner surface*.—Smooth, glabrous.

*Texture, lower/outer surface*.—Smooth, glabrous, with a few hairs.

Reproductive organs:

*Gynoecium*.—

*Pistil quantity*.—2.

*Pistil shape*.—Each style has a treadlike pistil shape.

*Length*.—0.2 cm.

*Style color*.—RHS 143B.

*Style length*.—0.15 cm.

*Stigma color*.—RHS 59B/C.

*Stigma shape*.—Spatulate.

*Ovary color*.—RHS 39A +RHS 152A.

*Ovary height*.—0.7 cm.

*Ovary width*.—0.2 cm.

*Androecium*.—

*Stamens, quantity*.—10.

*Stamens, shape*.—Threadlike.
*Color of filaments*.—RHS 143A.
*Length filaments*.—0.3 cm.
*Anther color*.—RHS 22C, mottled with anthocyanins of about RHS N34C.
*Anther length*.—0.1 cm.
*Anther shape*.—Oval.
*Color of pollen*.—RHS 12B.
*Pollen amount*.—Less to moderate.
*Fertility/seed set*.—Neither seed nor fruit production has been observed to date.
*Disease/pest resistance*.—Resistance to pathogens and pests common to *Saxifraga* has not been observed.
*Drought tolerance and cold tolerance*.—Hardy perennial. Tolerates high temperature to at least 30 degrees C. Tolerates low temperatures to minus 15 degrees C. No specific drought tolerance has not been observed.

What is claimed is:

1. A new and distinct variety of *Saxifraga* plant named 'SAXZ0013' substantially as illustrated and described herein.

* * * * *